United States Patent
Zver et al.

[11] Patent Number: 5,562,537
[45] Date of Patent: Oct. 8, 1996

[54] NETWORKED FUME HOOD MONITORING SYSTEM

[75] Inventors: Ronald J. Zver, Lake Zurich; Steven D. Jacob, Crystal Lake, both of Ill.

[73] Assignee: Landis & Gyr Powers, Inc., Buffalo Grove, Ill.

[21] Appl. No.: 439,354

[22] Filed: May 11, 1995

[51] Int. Cl.$^6$ .................................................. B08B 15/02
[52] U.S. Cl. ................................................ 454/61; 454/56
[58] Field of Search .................................. 454/58, 59, 61

[56] References Cited

U.S. PATENT DOCUMENTS

| | | |
|---|---|---|
| 4,040,042 | 8/1977 | Mayer . |
| 4,464,653 | 8/1984 | Winner . |
| 4,466,341 | 8/1984 | Grogan ........................................ 454/61 |
| 4,497,242 | 2/1985 | Moyer ........................................ 454/61 |
| 4,521,645 | 6/1985 | Carroll . |
| 4,552,059 | 11/1985 | Potter . |
| 4,557,184 | 12/1985 | Orii et al. . |
| 4,706,553 | 11/1987 | Sharp et al. . |
| 4,787,251 | 11/1988 | Kolodjski . |
| 4,805,441 | 2/1989 | Sides et al. . |
| 5,068,798 | 11/1991 | Heath et al. . |
| 5,090,303 | 2/1992 | Ahmed ........................................ 454/58 |
| 5,115,728 | 5/1992 | Ahmed et al. . |
| 5,205,783 | 4/1993 | Dieckert et al. . |
| 5,215,497 | 6/1993 | Drees ........................................ 454/61 |
| 5,405,241 | 4/1995 | Alcorn et al. ........................................ 454/61 |

OTHER PUBLICATIONS

Anemostat Products Division/Dynamics Corporation of America, "Face Velocity Control Systems" brochure.
Yamato, "Clean Benche Model ADS-130 Series" brochure.
Anemostat Products Division/Dynamics Corporation of America, "Envirotrak—A Laboratory Air Flow Control System from Anemostat", Aug. 1985.
Alnor Instrument Company, "Installed Fume Hood Air Flow Monitors", 1993.
Alnor Instrument Company, "Airgard Monitor Models 475, 435 & 405", 1993.
Alnor Instrument Company, "Digital Electronic Airgard Monitor Model 375D", 1993.

*Primary Examiner*—Harold Joyce
*Attorney, Agent, or Firm*—Greer, Burns & Crain, Ltd.

[57] ABSTRACT

A system for monitoring the operation of laboratory fume hoods includes a local area network for transferring data representing alarm conditions, and other special functions, to a building supervisory control system. The system has a calibrating capability which is adapted to build a database of the operating parameters of the fume hood which can be used to detect any degradation of the operation of the fume hood.

4 Claims, 8 Drawing Sheets

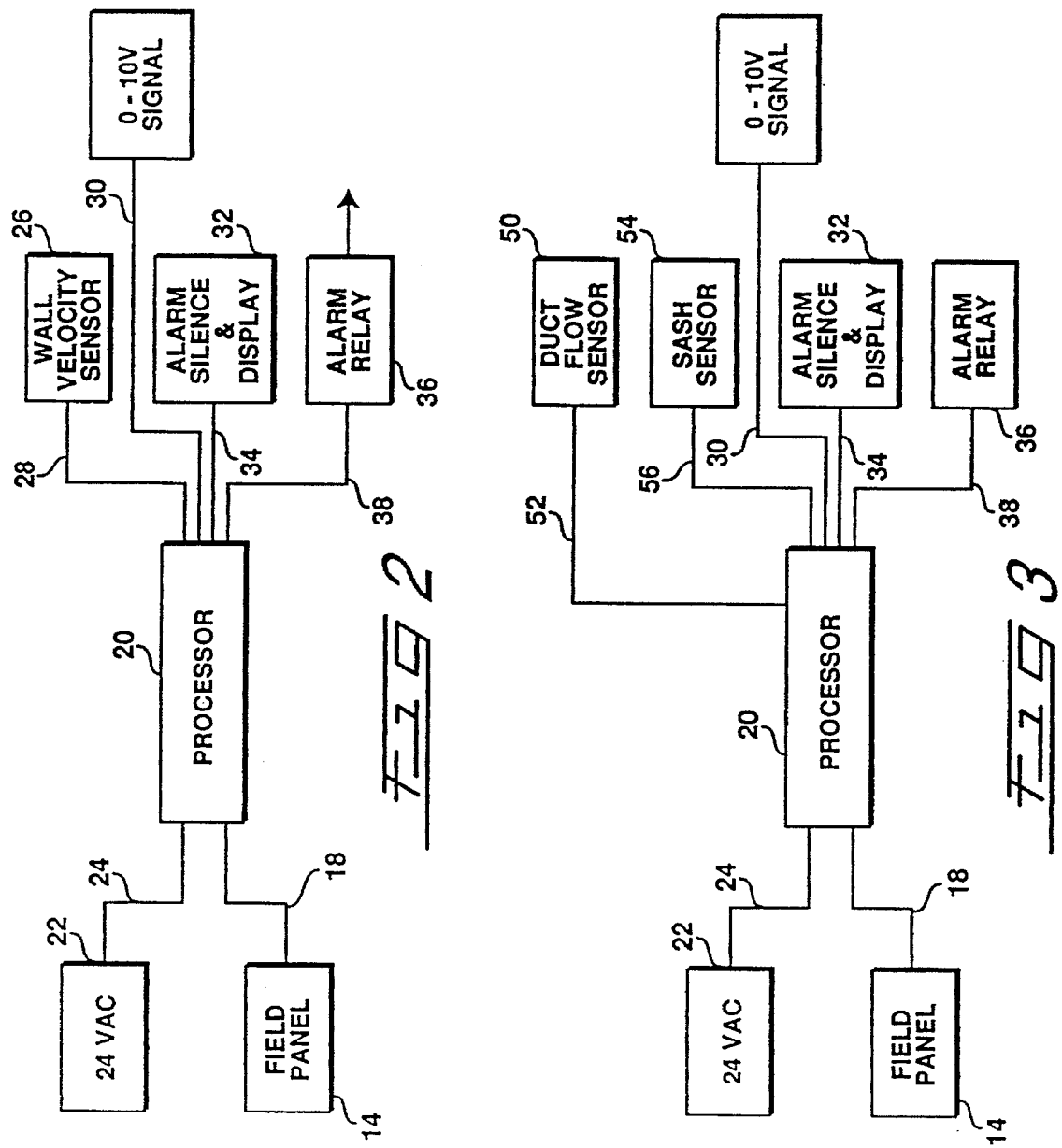

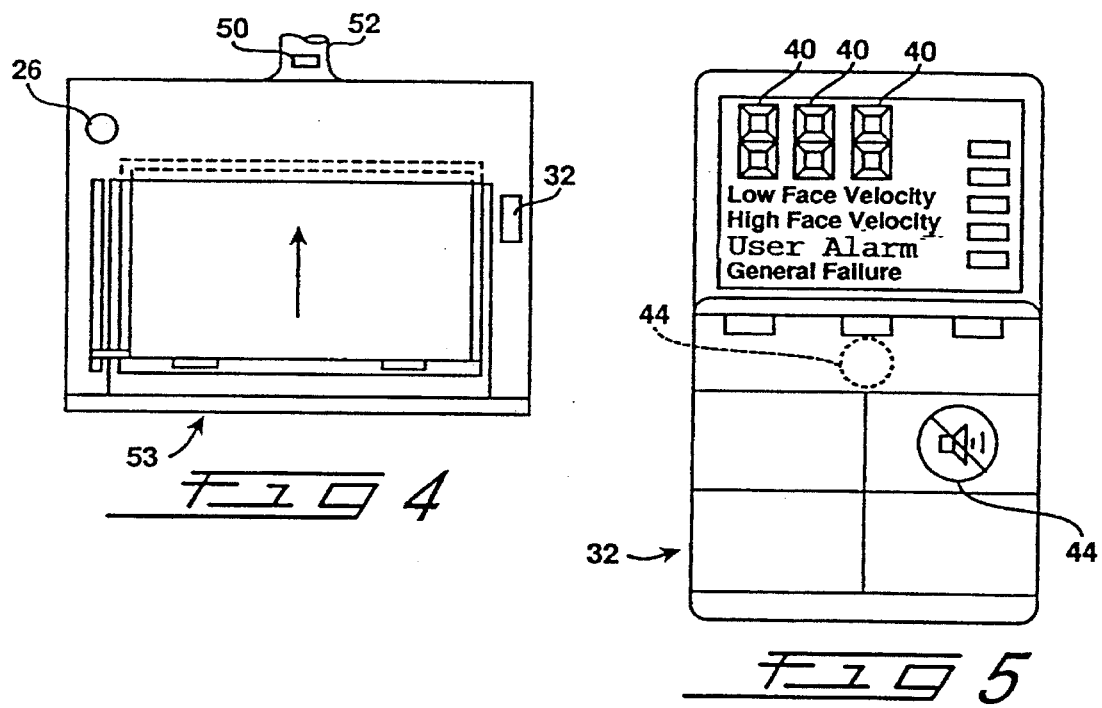
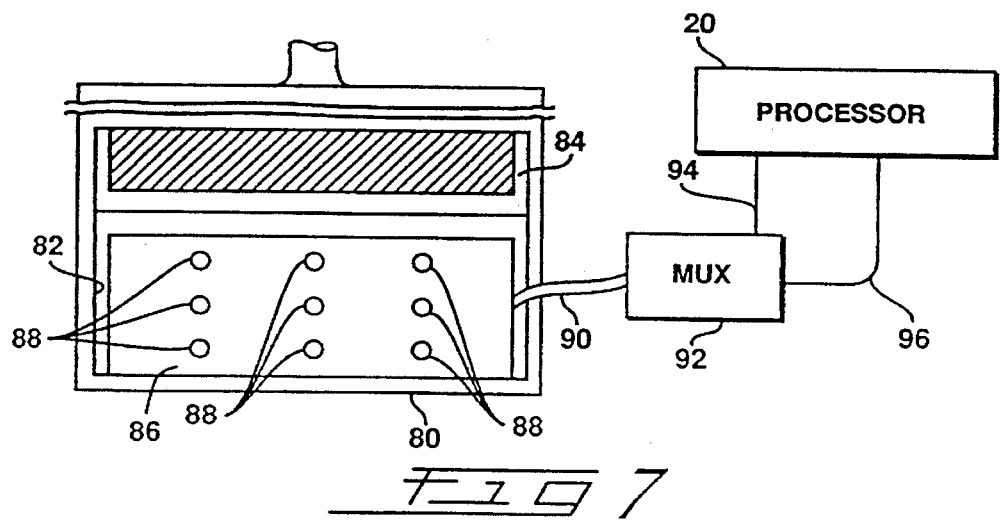

NETWORKED FUME HOOD MONITORING SYSTEM

The present invention generally relates to the control of the ventilation of laboratory fume hoods, and more particularly to a networked monitoring system for providing safety warnings related to such laboratory fume hoods.

Research and development work involving chemicals in a laboratory environment requires the use of fume hoods to confine the chemical fumes and thereby protect the individuals who are working in the laboratory. The fume hoods generally comprise an enclosure having a front opening and one or more movable doors adapted to cover the opening, but which can be opened to permit an individual to gain access to the interior of the enclosure for the purpose of performing experiments or other work. The enclosure is typically connected to a forced air exhaust system driven by a blower and the air from the fume hood is constantly being removed through the exhaust duct which carries any noxious fumes away so that an individual should not be exposed to the fumes while performing work in the hood.

Fume hood controllers which control the flow of air through the enclosure have become quite sophisticated in recent years and now are able to accurately maintain the desired flow characteristics to exhaust the fumes from the enclosure as a function of the desired average face velocity of the opening of the fume hood, regardless of the size of the uncovered opening. It should be understood that the volume of air that is required to maintain an average face velocity would necessarily have to increase as the opening is uncovered by moving the sash doors that are provided.

Fume hood controllers which accomplish this sophisticated operational control as well as other functions are disclosed in U.S. Pat. Nos. 5,090,303, 5,092,227, 5,115,728 and 5,090,304, all of which are assigned to the same assignee as the present invention. Fume hood controllers of the type disclosed in the aforementioned patents provide sophisticated control to maintain the face velocity relatively constant and do so by a combination of factors including a measurement of the position of the sash doors of the fume hood and a calculation of the uncovered area of the opening that results from the movement of the sash doors. The controller also controls the volume of air that is exhausted through the exhaust duct by either controlling the speed of a blower motor or by controlling the position of a damper located in the exhaust duct, either of which are effective to modulate the volume of air that is exhausted from the fume hood.

Such sophisticated controls are designed to provide the proper amount of flow to insure safety of the individuals who may be in the laboratory near the fume hoods, while also reducing to a minimum the amount of air that is expelled from the fume hoods and therefore the room. The less the amount of air removed from the room, the less air is necessary to replace the removed air. Obviously, if the fume hood is being operated during the winter and the replacement air has to be heated, substantial energy and therefore cost is required to heat the replacement air. Similarly, such energy considerations apply in cooling replacement air in the summer.

It is estimated that there are hundreds of thousands of fume hoods in existence in the United States at the present time and many of these fume hoods are installed without such sophisticated controllers. Many of these fume hoods are constant volume installations which remove a sufficient amount of air to maintain a safe condition regardless of whether the fume hood is opened or closed. While safety considerations are thereby satisfied when the fume hood is operating properly, more energy is expended in such an installation which results in increased operating costs. Because safety considerations are paramount, there is a need for monitoring systems which monitor the operation of the fume hoods even if they are constant volume type of installations.

Accordingly, it is a primary object of the present invention to provide an improved monitoring system for laboratory fume hoods.

Another object of the present invention is to provide such an improved monitoring system that is networked to a building supervisory control system so that a building superintendent will be immediately alerted in the event of a potentially dangerous condition having occurred in the operation of a fume hood.

Another object of the present invention is to provide such an improved monitoring system that provides a group of special functions based on the operation of the fume hood.

Still another object of the present invention lies in the provision for such a monitoring system which is relatively inexpensive in terms of its initial cost and installation, but which is effective to provide reliable information relating to the operation of the fume hood.

Another object of the present invention is to provide such an improved monitoring system which is effective to detect flow of air in the fume hood or in the exhaust duct connected to the fume hood, which is then processed to provide a face velocity value which can trigger alarm signals when the face velocity is outside of a predetermined bandwidth.

Yet another object of the present invention is to provide an improved monitoring system that also has the capability of determining the face velocity at a plurality of spaced locations in the opening of the fume hood, sending the data on a network to the building supervisory control system or other location, and then recording the data in a memory device to thereby build a database of operation of the fume hoods over time.

Other objects and advantages will become apparent upon reading the following detailed description, while referring to the attached drawings, in which:

FIG. 2 is a schematic block diagram of one embodiment of the network fume hood monitoring system of the present invention;

FIG. 3 is another embodiment of the networked fume hood monitoring system of the present invention;

FIG. 4 is a front view of a fume hood having a single vertically movable sash which is representative of fume hoods in which the present invention may be installed;

FIG. 5 is a front view of a display that may be provided at the fume hood, which display is a part of the present invention;

Figure 1:
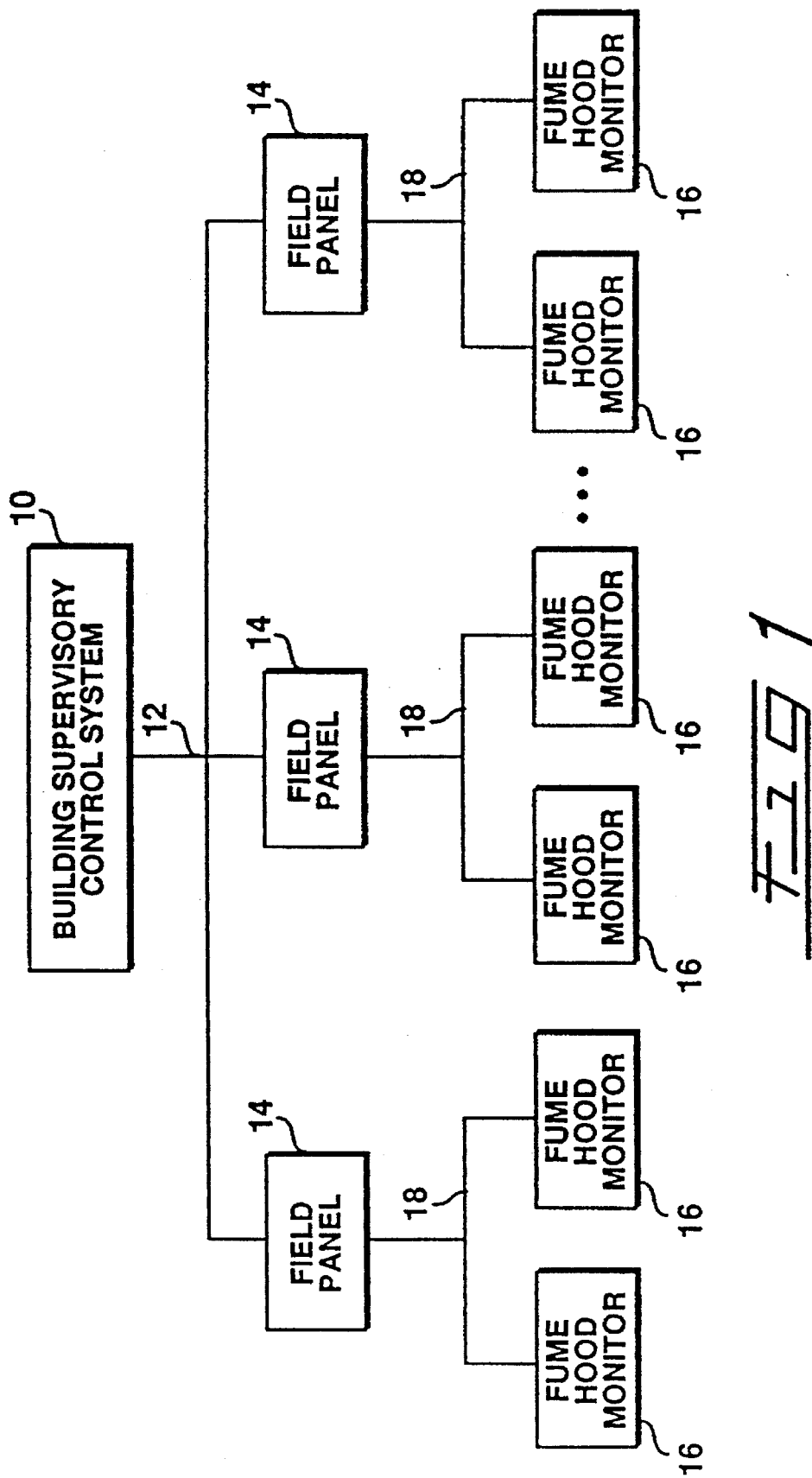
FIG. 1 is a schematic block diagram of a building supervisory control system shown together with a number of fume hood monitoring systems embodying the present invention.

FIGS. 6a, 6b, 6c, 6d and 6e together comprise an electrical schematic diagram of specific circuitry that can be used to carry out the operation of the block diagram shown in FIGS. 2 or 3; and, FIG. 7 is a block diagram of an embodiment for performing a calibration traverse of the opening of a fume hood for use in building a database of the performance of individual fume hoods.

DETAILED DESCRIPTION

Broadly stated, a monitoring system for laboratory fume hoods implements a communication capability for networking the monitored information to a central location. In the preferred embodiment, the central location comprises a building supervisory control system which controls a plurality of special functions. The monitoring system includes hardware to measure predetermined parameters related to the fume hood and, based on the measured predetermined parameters related to the fume hood, notify the central location to activate one of a plurality of special functions.

The hardware which measures the predetermined parameters also determines, based on the measured predetermined parameters related to the fume hood, whether an emergency condition in the fume hood exists. The measured predetermined parameters related to the fume hood include, but are not limited to, the minimum and maximum face velocity of the fume hood. In the preferred embodiment, the special functions include, but are not limited to, turning on/off lights throughout the building based on a determined emergency condition in the fume hood, activating an alarm for the entire building based on a determined emergency condition in the fume hood and providing notification to a superintendent as to whether the fume hood is or is not in use.

The system of the present invention is also adapted to monitor the flow of air through an exhaust duct to which the fume hood is connected or to detect the differential pressure between the inside of the fume hood and the outside thereof or measure a representative sample of the flow of air from the room into the fume hood. This can be accomplished by means of a differential pressure sensor or a through-the-wall sensor which produces a signal that is indicative of the face velocity of the fume hood during operation. The system then calculates the face velocity and by means of a processing means, calculates a bandwidth of values which represents a safe operating range for the fume hood.

While the preferred embodiment for the communication link is a two wire connection from the fume hood monitoring system to the building supervisory control system or other central location, other types of communication links are also within the scope of the present invention and may include multiple wire communication links, i.e., in excess of two wires, a fiber optic communication link, a coaxial connection, and even wireless communication, such as an RF transmission link or an infrared radiation communication link.

The monitoring system preferably has a single enclosure display module which provides a numerical indication of the face velocity of the hood, an audible alarm, a relay providing a set of contacts to indicate an alarm to a supervisory control system as well as an alarm light. The display module also preferably has an audible alarm silencing pushbutton which enables an individual to turn off the alarm. This event is also preferably applied to the network for communication to the building supervisory control system in the form of an acknowledgement signal. Such an acknowledgement signal indicates that someone is present in the laboratory and is aware of the alarm condition at the local level.

The system is also adapted to provide a plurality of face velocity signals in a face velocity traverse operation which is typically done 4 times a year. The readings are taken at various spaced apart locations within the fume hood opening, preferably at least nine locations, and these values are then communicated on the local area network to a memory device where a database of fume hood performance is accumulated over time. The database provides a baseline for operation and enables individuals to detect degradation of the operation of particular fume hoods, so that maintenance can be performed.

Turning now to the drawings, and particularly FIG. 1, there is shown an overall schematic block diagram of a building supervisory control system, indicated generally at 10, which preferably has a central control console (not shown) with a computer which is typically manned by an operator and controls the building heating, ventilating and air conditioning equipment and sometimes fire alarm, security and other special functions that may be provided in the building.

The system 10 has a local area network (LAN) indicated generally by line 12 that extends to field panels 14 that are typically located throughout the building for interconnecting the system 10 to the HVAC equipment, such as dampers and the like, that are located in the building. Since the present invention monitors laboratory fume hoods, the building quite likely has one or more laboratory rooms having fume hoods installed in the rooms. There are a number of fume hood monitors 16 shown in FIG. 1 which are connected to the field panel via the local area network line 18 which extends from the monitoring system of the present invention to the field panel. By virtue of the local area network lines 12, the monitoring system is also connected to and in communication with the building and supervisory control system 10.

One embodiment of the monitoring system of the present invention is shown in FIG. 2 and includes a processor 20 that is powered by a 24 volt a.c. source 22 via line 24 and the processor has the LAN connection 18 to the field panel 14 in the manner previously described in connection with FIG. 1. The processor 20 is also connected to a wall velocity sensor 26 via line 28 and receives a signal that is representative of the face velocity in the form of an analog voltage signal that is applied to the processor 20 which converts it to a digital signal for processing. The wall velocity sensor 26 identified in FIG. 2 is preferably a through the wall sensor, but can be a differential pressure sensor. The processor 20 is also connected to a display module 32 via line 34 and the display module is adapted to display the face velocity as well as other conditions to be described. Provision is also made for providing an alarm relay signal shown at 36 which is connected to the processor via line 38 and this alarm relay may be used to operate an auxiliary central or local alarm.

The wall velocity sensor 26 is preferably a through-the-wall sensor, but can be a differential pressure sensor as previously stated, which is installed on the fume hood at a location as shown in FIG. 4, with the through-the-wall velocity sensor or differential pressure sensor requiring an opening in the wall of the fume hood and means for measuring the flow or pressure of the outside relative to the inside of the fume hood. Of course, it should be understood that the location of the sensor 26 may be at the location shown or at some other location on the hood. Such an indication is representative of the face velocity of the fume hood when it is in a steady state condition. When flow rates change rapidly, such as if the sash door is opened, then the through-the-wall sensor or differential pressure sensor is not particularly accurate until it has reached a steady state condition.

Through-the-wall sensors of the type that are preferred, are also known as anemometers, and generally comprise a pair of temperature dependent resistive elements or thermistors, one of which is generally heated to a predetermined value above the ambient temperature. The heated element is thereby cooled by air flow at a rate that is proportional to the flow rate, and the power required to maintain the heated element at the elevated temperature provides an electrical signal that is representative of the flow rate. Such anemometer sensors are available from Fenwall, Alpha Thermistors, TSI, Kurz and Sierra. Differential pressure transmitters in the range of 0.0015 and 0.0030 inches of water may also be used and are available from Air Monitor and MKS.

With the embodiment of FIG. 2, the processor 20 monitors the signal from the sensor 26 and after calibration is able to determine upper and lower limits which establish a bandwidth defining a safe operating range. The lower face velocity is preferably approximately 60 feet per minute (fpm) and the limit is preferably approximately 500 fpm. In the preferred embodiment, the 60 fpm value is user selectable. As long as the face velocity is within these limits, then it is considered to be safe. If the face velocity falls below 60 fpm or exceeds 500 fpm, then the processor 20 will issue an alarm signal on lines 34 and 38 which will cause an audio alarm and also a visual alarm to occur. It should be apparent that both an audio and visual alarm is not absolutely necessary, but is preferred.

The display module 32 is shown in FIG. 5 and preferably has a three digit LCD display indicated at 40 as well as a "low face velocity" readout, a "high face velocity" readout, an "user alarm" readout and a "general failure" readout. In addition to displaying the face velocity numerically, an alarm condition produced by either a high or low face velocity results in one of these indicators to be illuminated. The display module 32 also has an alarm horn indicated at 42 and an alarm silence pushbutton 44 located on the display. If the horn is being sounded and an operator is present and knows what is occurring, the operator can push the button 44 to expel the alarm. By operating the pushbutton 44, an alarm acknowledgement signal is thereby sent to the processor 20 which communicates that data to the field panel and to the supervisory control system 10 so that an acknowledgement of the alarm condition is provided.

The processor 20 preferably communicates information on the local area network lines 18 which includes an address identifying the particular fume hood that is sending the information, data indicating an alarm condition if that event has occurred, as well as the face velocity in a digital signal representing feet per minute. It also will provide the alarm acknowledgement signal as well as a signal indicating the value of the voltage of the velocity sensor or differential pressure sensor itself.

The processor 20 is adapted to be able to calibrate the wall velocity sensor or the differential pressure sensor if it is used, and depending upon the particular fume hood, a one volt signal may be representative of 60 fpm or it may be 100 fpm. In any event, the calibration is straightforward and can be relatively easily accomplished by one of ordinary skill in the art.

Another embodiment of the present invention is shown in FIG. 3 and it has similar components such as the processor 20, line 24, the analog signal on line 30, the 24 volt a.c. source 22, the field panel 14 and LAN connection 18 as well as the alarm silence and display 32, the alarm relay 36 and lines 38 and 34. However, there is no through-the-wall sensor 26 or fume hood differential pressure sensor in this embodiment, but rather a duct flow sensor 50 that is connected to the processor via line 52 and a sash sensor 54 that is connected to the processor via line 56.

Referring to FIG. 4, the duct flow sensor 50 is located in an exhaust duct 52 of the illustrated fume hood, indicated generally at 53, and the duct flow sensor 50 provides a differential pressure measurement that can be used to calculate the volume of air of the fume hood. The range of the sensor 50 is preferably about 0.5 to 1.0 inch water column. More particularly, the duct velocity is the square root of the differential pressure measurement multiplied by a scaling constant and this duct velocity is then multiplied by the duct area to calculate the air volume through the fume hood. Using the sash sensor inputs, an open face area can be calculated, and by using the following equation, a face velocity can be derived: face velocity = air volume/face area. If the sash sensors are not used, then a flow sensor can be used by itself to monitor the flow through the fume hood. Without the sash sensors, a face velocity cannot be displayed but alarms can be triggered for flow rates that are too high or too low.

The differential pressure measurement is typically an inches of water column reading with an output of preferably 0 to 20 milliamps and it is applied to the processor 20. The processor 20 shown in this embodiment also preferably provides a safe operating bandwidth and also issues an alarm signal if the face velocity falls below the 60 foot per minute value or exceeds the 500 foot per minute value.

If an alarm condition occurs, a relay within the display module 32 closes, and the supervisory control system 10 is notified of the alarm condition. When an alarm condition occurs, the supervisory control system 10 also receives, via the local area network communication link 18, the duct velocity signal itself, the address of the fume hood and also an application number. In this manner, personnel at the supervisory control system 10 are alerted to potentially dangerous situations automatically.

Figure 6A:
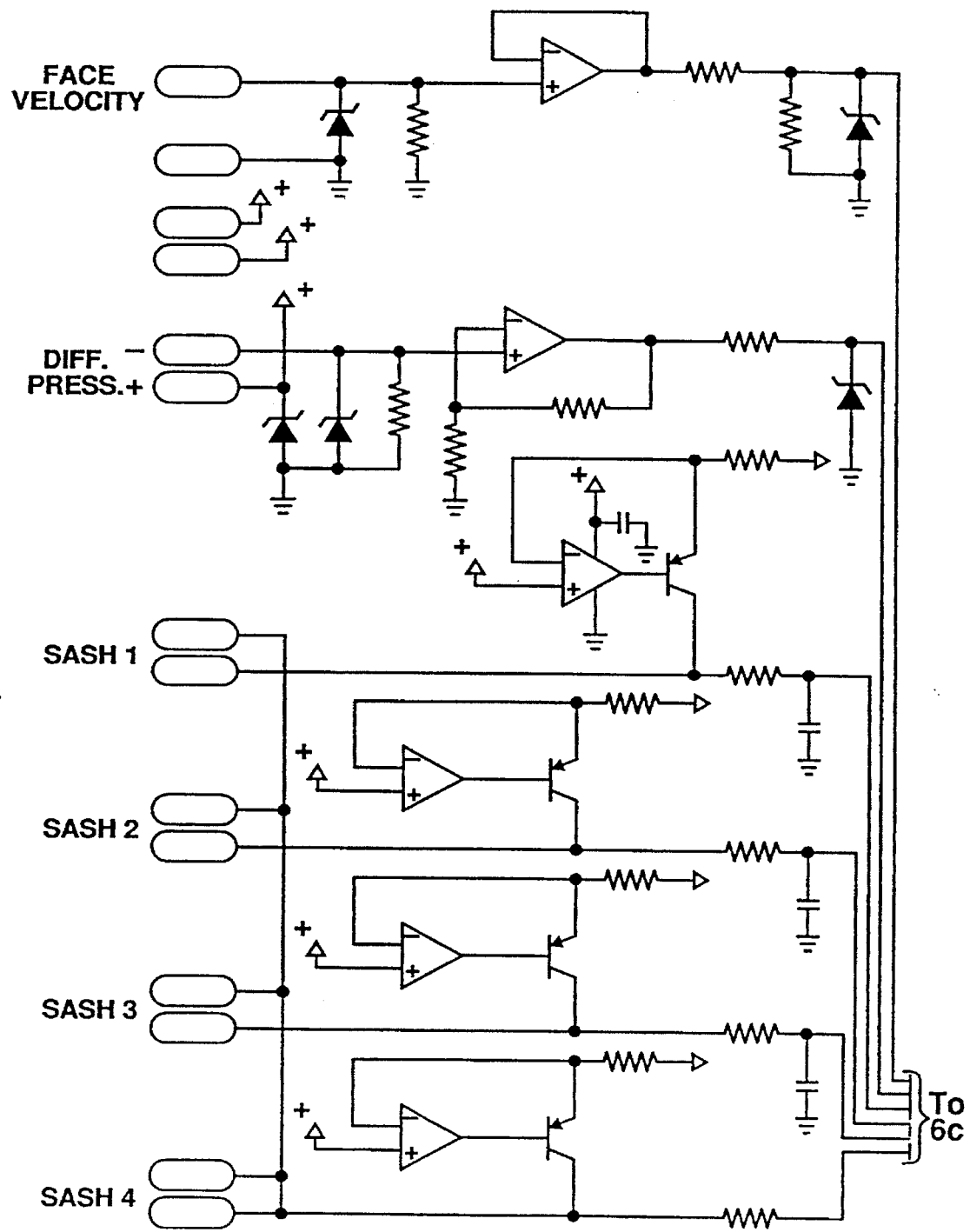
FIG. 6 is a schematic illustration of the matter in which FIGS. 6a through 6e can be combined to form a single electrical schematic diagram.
Figure 6B:
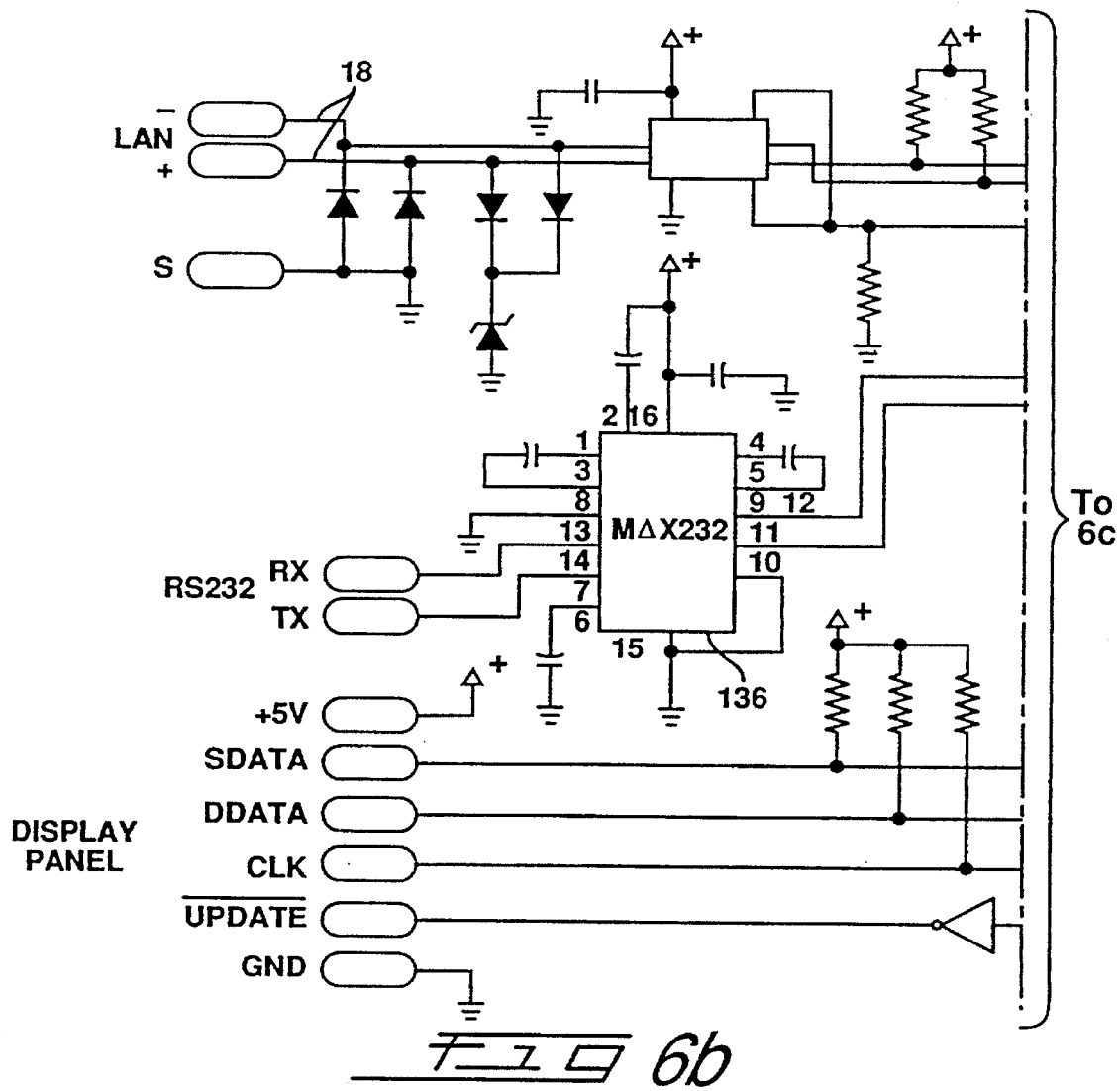
Figure 6:
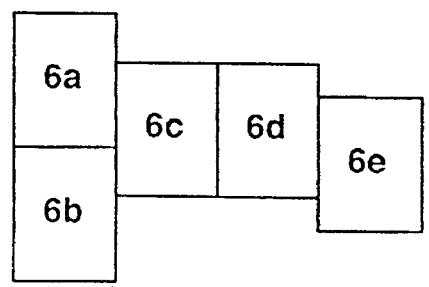
Figure 6C:
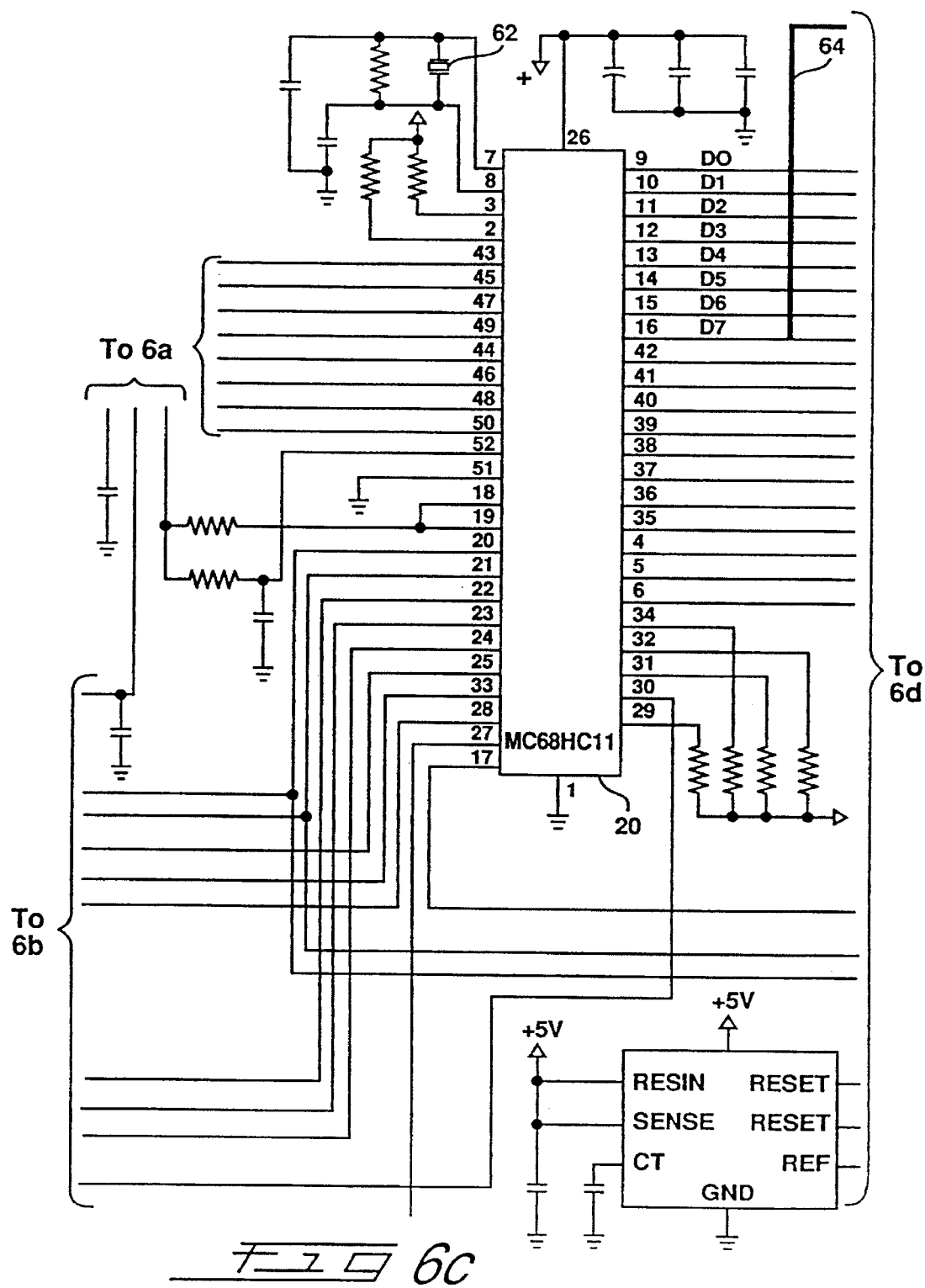
Figure 6D:
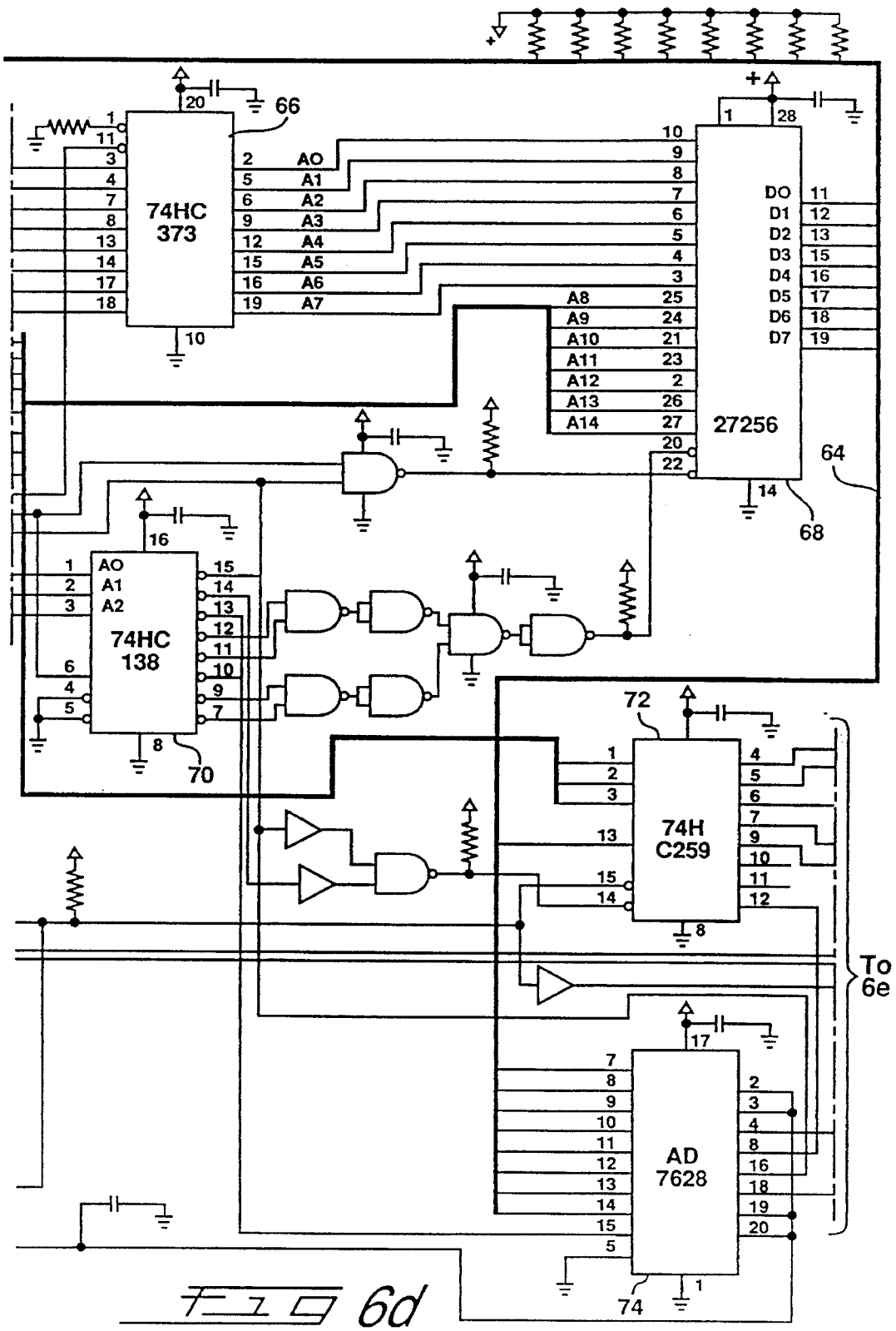
Figure 6E:
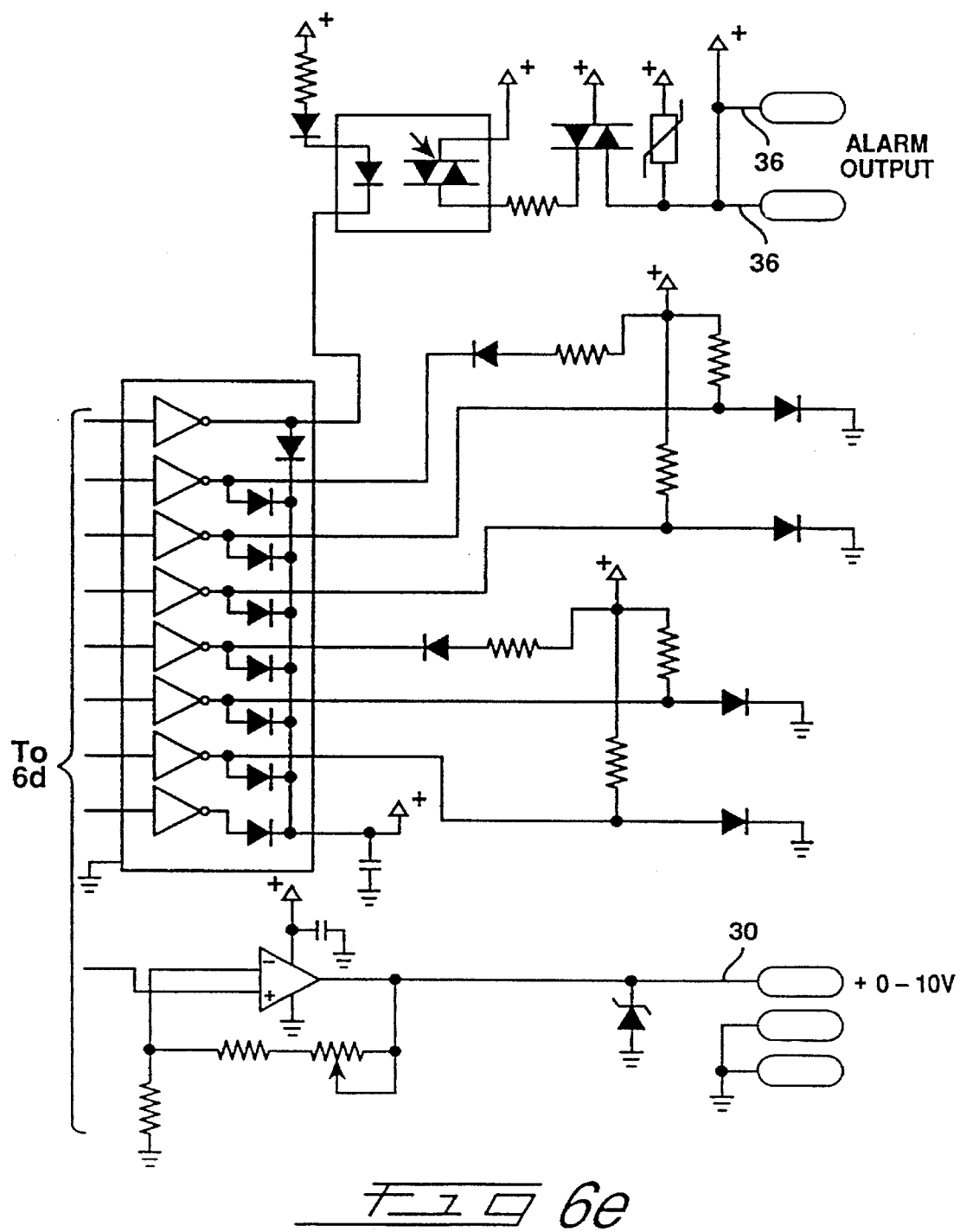

Referring to the composite electrical schematic diagram of the circuitry of the fume hood monitoring system, if the separate drawings FIGS. 6a, 6b, 6c, 6d and 6e are placed adjacent one another in the manner shown in FIG. 6, the total electrical schematic diagram of the fume hood controller is illustrated. The circuitry is driven by a microprocessor 20 as shown in FIG. 6c which is preferably a Motorola MC68HC11 which is preferably clocked at 8 MHz by a crystal 62. The microprocessor 20 has a databus 64 that is connected to a tri-state buffer 66 (see FIG. 6d) which in turn is connected to an electrically programmable read only memory 68 that is also connected to the databus 64. The EPROM 68 has address lines A0 through A7 connected to the tri-state buffer 66 and also has address lines A8 through A14 connected to the microprocessor 20. The circuitry includes a three-to-eight bit multiplexer 70, a data latch 72, and a digital-to-analog converter 74 which is adapted to provide the auxiliary 0 to 10 volt analog output on line 30.

In accordance with another important aspect of the present invention, the monitoring system of the present invention is also adapted to provide another feature for the fume hoods and that is to calibrate and perform maintenance of the fume hood and also to utilize the local area network to build a database of the operation of each fume hood for use in determining whether the fume hood is operating properly or is experiencing degradation in its operation.

It is common practice to perform a face velocity traverse of the fume hood to indicate whether the fume hood is operating safely. Such a traverse is used on both constant volume and variable volume fume hoods and is typically performed at intervals of approximately three months.

Referring to FIG. 7, a fume hood 80 is shown and it has an opening 82 that has a sash door 84 present but in a raised position. Within the uncovered portion of the opening is a sensor grid structure 86 that has a total of 9 sensors 88 positioned in a matrixed arrangement.

Velocity measurements are taken at preferably at least nine locations in the fume hood opening, with none of the probes being closer than approximately six inches from any edge of the opening. By taking nine simultaneous measurements, any unevenness in the flow can be detected and recorded. It is typical to average the velocity values over a period of time, for example, 10 to 15 seconds. The signals from each of the probes are applied on lines 90 which extend to a multiplexing switch 92 controlled by the processor 20 via line 94 for sequentially applying the signals from each sensor 88 to the processor 20 through a serial port via line 96. Alternatively, a separate processor can be utilized to receive the velocity signals from the various sensors 88, which can then average them and then apply them to the processor 20.

The processor 20 is then adapted to send these velocity signals to the supervisory control system 10 which preferably receives them and records them in memory to thereby provide a database over time indicating the performance of the fume hood. Inspection of the data over time may indicate a degradation of the fume hood operation, which can be used by maintenance personnel to make any necessary modifications or corrections. For example, a belt on a blower may be slipping or a filter may be loaded to the extent that air flow is impaired. The data may provide a history of performance and maintenance that may become important in a legal proceeding in the event that damage or injury occurs in the laboratory.

From the foregoing, it should be appreciated that a superior monitoring system has been shown and described which has the capability of monitoring the face velocity and flow of the fume hoods during operation and can trigger alarm conditions in the event that the detected or monitored face velocity or flow goes outside of a predetermined safety bandwidth of values. The monitoring system has the advantage in that it is inexpensive in terms of its initial cost as well as installation, yet it has the capability of reporting relevant information relating to the operation of the fume hoods to a central location, such as a building supervisory control system. The monitoring system also has the ability to perform calibration and status checks of a plurality of points in the fume hood opening and this information can be sent on the local area network to a central repository where it can be recorded in memory and be used to provide a record of the operation of the fume hood which can be important in detecting degradation of the operation of the fume hood.

While various embodiments of the present invention have been shown and described, it should be understood that various alternatives, substitutions and equivalents can be used, and the present invention should only be limited by the claims and equivalents thereof.

Various features of the present invention are set forth in the following claims.

What is claimed is:

1. A monitoring system for laboratory fume hoods, the monitoring system implementing a communication capability for networking the monitored information to a central location of a building supervisory control system, the central location controlling a plurality of special functions consisting of turning on/off lights throughout the building based on a determined emergency condition in the fume hood, activating an alarm for the entire building based on a determined emergency condition in the fume hood and providing notification to a superintendent as to whether the fume hood is or is not in use, the monitoring system comprising:

means for measuring predetermined parameters related to the fume hood and for determining an emergency condition in the fume hood based on said measured predetermined parameters; and means, based on the measured predetermined parameters related to an emergency condition in the fume hood, for notifying the central location to activate one of said plurality of special functions.

2. The monitoring system of claim 1 wherein said means for measuring predetermined parameters related to the fume hood further comprises means for measuring the minimum and maximum face velocity of the fume hood.

3. A monitoring system for laboratory fume hoods, the monitoring system implementing a communication capability for networking the monitored information to a building supervisory control system, the building supervisory control system controlling a plurality of special functions consisting of turning on/off lights throughout the building based on a determined emergency condition in the fume hood, activating an alarm for the entire building based on a determined emergency condition in the fume hood and providing notification to a superintendent as to whether the fume hood is or is not in use, the monitoring system comprising:

means for measuring at least one of either the minimum face velocity of the fume hood or the maximum face velocity of the fume hood to determine if an emergency condition in the fume hood exists; and means, based on the measurement, for notifying the building supervisory control system to activate one of said plurality of special functions.

4. A monitoring system for laboratory fume hoods, the monitoring system implementing a communication capability for networking the monitored information to a building supervisory control system, the building supervisory control system controlling a plurality of special functions, the monitoring system comprising:

means for measuring at least one of either the minimum face velocity of the fume hood or the maximum face velocity of the fume hood to determine if an emergency condition in the fume hood exists; and means, based on the measurement, for notifying the building supervisory control system to activate one special function from the group of special functions consisting of turning on/off lights throughout the building based on a determined emergency condition in the fume hood, activating an alarm for the entire building based on a determined emergency condition in the fume hood and providing notification to a superintendent as to whether the fume hood is or is not in use.

* * * * *

UNITED STATES PATENT AND TRADEMARK OFFICE
CERTIFICATE OF CORRECTION

PATENT NO. :   5,562,537
DATED      :   October 8, 1996
INVENTOR(S):   Zver et al.

It is certified that error appears in the above-indentified patent and that said Letters Patent is hereby corrected as shown below:

On the title page, item [56[:

In "References Cited" section, under "Other Publications" insert

--Alnor Instrument Company, "Electric AIRGARD Moniter Model 375", 1993--.

Signed and Sealed this

Twelfth Day of August, 1997

Attest:

BRUCE LEHMAN

Attesting Officer

Commissioner of Patents and Trademarks